(12) United States Patent
Wildgruber et al.

(10) Patent No.: US 11,883,247 B2
(45) Date of Patent: Jan. 30, 2024

(54) MULTI-PART MARKER

(71) Applicant: Brainlab AG, Munich (DE)

(72) Inventors: Josef Wildgruber, Ilmmunster (DE); Alexander Druse, Munich (DE); Tilo Callenbach, Schaffhausen (CH); Christian Classen, Tengen (DE)

(73) Assignee: Brainlab AG, Munich (DE)

( * ) Notice: Subject to any disclaimer, the term of this patent is extended or adjusted under 35 U.S.C. 154(b) by 1190 days.

(21) Appl. No.: 15/335,167

(22) Filed: Oct. 26, 2016

(65) Prior Publication Data

US 2017/0042635 A1 Feb. 16, 2017

Related U.S. Application Data

(62) Division of application No. 13/817,147, filed as application No. PCT/EP2010/061894 on Aug. 16, 2010, now Pat. No. 9,517,108.

(51) Int. Cl.
*A61B 90/00* (2016.01)
*B29D 11/00* (2006.01)
(Continued)

(52) U.S. Cl.
CPC .............. *A61B 90/39* (2016.02); *A61B 34/20* (2016.02); *B29D 11/00605* (2013.01);
(Continued)

(58) Field of Classification Search
CPC . A61B 90/39; A61B 34/20; A61B 2034/2055; A61B 2090/3983;
(Continued)

(56) References Cited

U.S. PATENT DOCUMENTS 1,946,408 A * 2/1934 Loudy .................... B64C 1/061
403/64
5,893,214 A * 4/1999 Meier .................. G01B 11/005
33/293
(Continued)

FOREIGN PATENT DOCUMENTS

DE 102008022254 A1 11/2009
WO 01/53096 A1 7/2001
(Continued)

OTHER PUBLICATIONS

WO2008104548A1 English translation (Year: 2008).*
(Continued)

*Primary Examiner* — Jason M Ip
*Assistant Examiner* — Renee C Langhals
(74) *Attorney, Agent, or Firm* — Tucker Ellis LLP

(57) ABSTRACT

A multi-part medical marker (1) comprising a marker core consisting of at least two corresponding parts (2a, 2b) and comprising a detectable surface, wherein the surface is substantially formed from a detectable coating (4) which is applied to the surface (3) of the parts (2a, 2b) of the marker core (2). An apparatus for producing a medical marker comprising a marker core ("2) and a detectable surface, comprises: —a first feeding device (16) for providing the marker core (2); —an application device (17) for applying a detectable layer to the surface (3) of the marker core (2); and—a transport device (18) for transporting the marker core (2) within the apparatus.

9 Claims, 5 Drawing Sheets

(51) Int. Cl.
 *A61B 34/20* (2016.01)
 *A61B 17/00* (2006.01)
(52) U.S. Cl.
 CPC .............. *A61B 2017/00526* (2013.01); *A61B 2034/2055* (2016.02); *A61B 2090/3983* (2016.02); *Y10T 29/49771* (2015.01); *Y10T 29/49826* (2015.01); *Y10T 29/49863* (2015.01); *Y10T 29/53539* (2015.01)
(58) Field of Classification Search
 CPC .... A61B 2017/00526; B29D 11/00605; Y10T 29/53539; Y10T 29/49826; Y10T 29/49863; Y10T 29/49771; G02B 5/12; G02B 5/126
 See application file for complete search history.

(56) References Cited

U.S. PATENT DOCUMENTS

| | | | | |
|---|---|---|---|---|
| 6,937,696 | B1* | 8/2005 | Mostafavi | A61B 5/113 378/65 |
| 2003/0174401 | A1* | 9/2003 | Brunner | G01C 15/02 359/534 |
| 2004/0005088 | A1* | 1/2004 | Jeung | A61N 5/1049 382/128 |
| 2005/0015005 | A1* | 1/2005 | Kockro | A61B 34/20 600/427 |
| 2006/0073307 | A1* | 4/2006 | Rossner | G02B 5/128 428/143 |
| 2006/0142656 | A1* | 6/2006 | Malackowski | A61B 90/36 600/424 |
| 2006/0237124 | A1* | 10/2006 | Bartoli | G02B 5/128 156/247 |
| 2007/0167708 | A1 | 7/2007 | Blumhofer et al. | |
| 2010/0034530 | A1* | 2/2010 | Son | G03B 17/00 396/427 |
| 2011/0286098 | A1* | 11/2011 | Hauri | A61B 34/20 359/543 |
| 2012/0050862 | A1* | 3/2012 | Rossner | G02B 5/122 359/529 |

FOREIGN PATENT DOCUMENTS

| | | | |
|---|---|---|---|
| WO | 03/020146 A2 | 3/2003 | |
| WO | 2006002559 A1 | 1/2006 | |
| WO | WO-2006002559 A1 * | 1/2006 | ............. G02B 5/128 |
| WO | 2007/090288 A1 | 8/2007 | |
| WO | WO-2008104548 A1 * | 9/2008 | ............. A61B 90/39 |

OTHER PUBLICATIONS

International Search Report for PCT/EP2010/061894 dated Aug. 26, 2011, pp. 1-6.
Written Opinion of the International Searching Authority for PCT/EP2010/061894, pp. 1-6.
International Preliminary Report on Patentability for PCT/EP2010/061894, pp. 1-7.

* cited by examiner

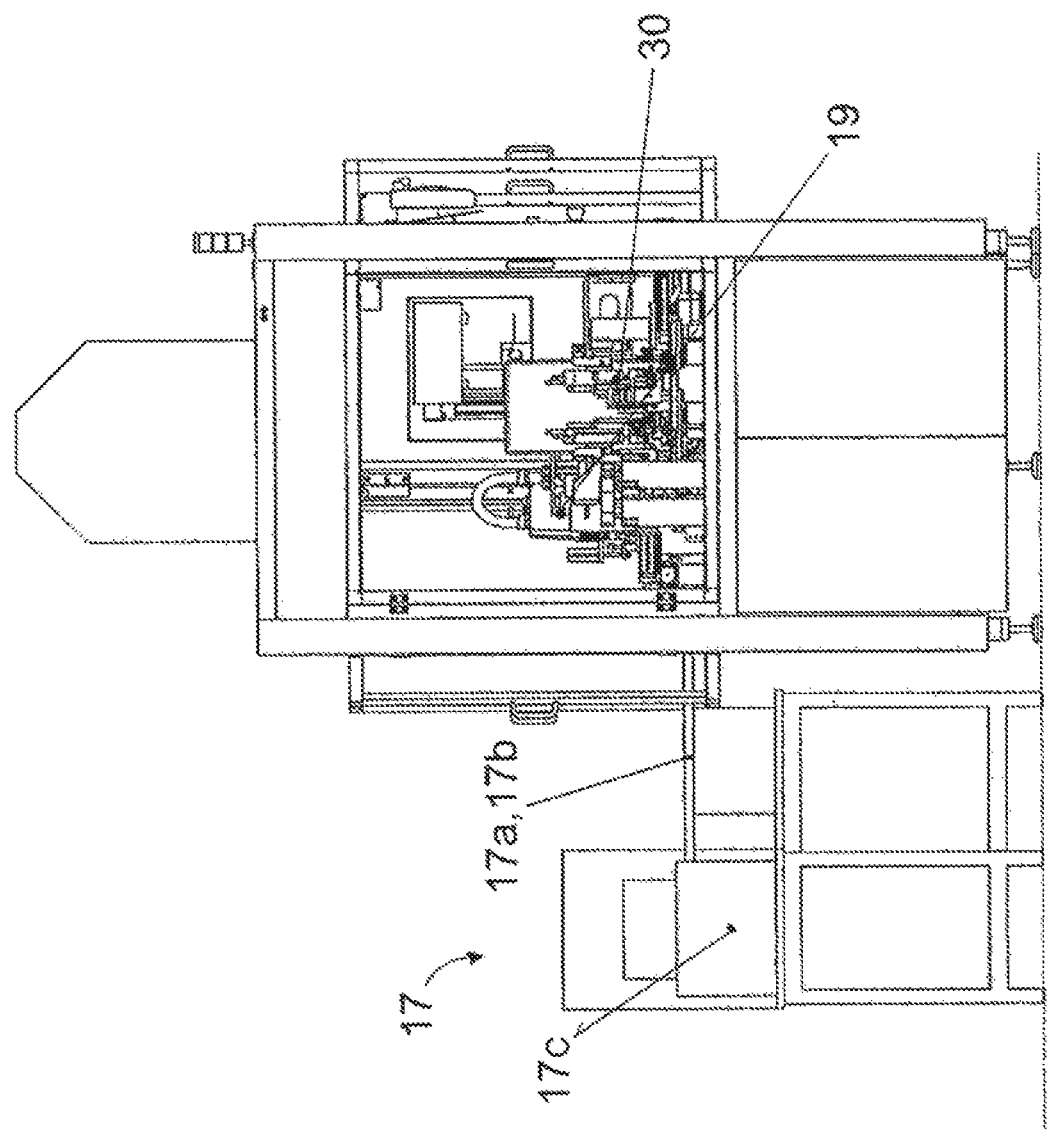

MULTI-PART MARKER

This application is a divisional of U.S. patent application Ser. No. 13/817,147 filed Feb. 15, 2013 that was a U.S. National Phase of International Application No.: PCT/2010/061894 filed Aug. 16, 2010, the entire contents of which are incorporated herein by reference.

A medical marker of the example embodiment comprises a marker core and a detectable surface.

Medical instruments and devices can be detected, and their position and orientation determined, by optical tracking systems with the aid of medical markers which are attached to the instruments and devices. Said markers can be reflective markers, which means that they reflect light, in particular UV light, emitted by a light source. Such markers usually have a spherical shape. If at least two cameras capable of sensing the light reflected by these markers are provided, then the spatial position of each marker can be determined by triangulation, wherein the spatial position and orientation of an object can also be determined if at least three markers are fixedly attached to said object.

To date, medical markers have been produced manually by applying a reflective coating to the surface of the spherical marker. However, several disadvantages are incurred when manually manufacturing markers, such as uncontrolled microbiological contamination of the markers, inconsistent product quality due to an inability to validate processes, inconsistent supply quantities and high costs.

Fully automated manufacturing is therefore desirable. However, it is almost impossible to handle marker spheres and apply a reflective coating, in particular a reflective laminar material, to the surface of a marker sphere in an automated process.

It is an object of the present invention to produce a medical marker comprising a reflective surface or retro-reflective surface, respectively, using a fully automated process.

The above problems are overcome by the subject-matter of independent claim 1, wherein the subject-matter of the dependent claims defines preferred embodiments of the present invention.

A first aspect disclosed herein relates to a method for producing a multi-part medical marker comprising a marker core consisting of at least two corresponding parts and comprising a detectable surface, wherein the parts of the marker core are provided first, a detectable layer is applied to the surface of the parts of the marker core, and the parts of the marker core are joined together to form a marker comprising a detectable surface.

One advantage over the prior art is the fact that the marker core comprises several corresponding parts, wherein each of the corresponding parts can be individually provided with a detectable layer and the marker is formed by joining together the parts of the marker core which already then comprise a detectable surface.

If a laminar material is used as a detectable layer, the laminar material can be prevented from wrinkling by applying it to the surface of several parts of the marker core.

In accordance with a preferred embodiment, the parts of a marker core are injection-moulded. However, any suitable manufacturing method known to a skilled person can be used to produce the parts of the marker core.

In accordance with another preferred embodiment, a laminar material is provided in order to serve as a detectable layer which is applied to the surface of the parts of the marker core. This laminar material can have the form of a ribbon-like material which can be wound onto a reel. Specifically, the laminar material can be a textile strip, namely a cotton-based fabric which is elastic to a certain degree. At least one of the two sides of the laminar material can be a detectable side, in particular a reflective side.

Since the laminar material can become contaminated, it can be cleaned before being applied to the parts of the marker core. In accordance with a preferred embodiment, the laminar material is vacuum-cleaned before being applied to the marker core, such that contaminants on the laminar material are removed from the laminar material.

Moreover, the surface quality of the detectable side of the laminar material can be determined before the laminar material is applied to the marker core. If the surface of the laminar material has defects, the reflective marker will not reflect light properly, such that the position and orientation of the object determined by locating a number of markers will be inaccurate. If certain regions of the laminar material have an unacceptable number of defects, the defective region of the laminar material can be cut off and discarded. In order to determine whether or not the laminar material is defective, light can be applied to the reflective side of the laminar material, wherein said light will not be reflected by defective regions of the reflective side.

Before the laminar material is applied to the surface of a part of the marker core, a part of the laminar material is cut off, wherein said part is larger than the surface of the part of the marker core. This ensures that the whole surface of the part of the marker core will be covered by the laminar material.

In accordance with another preferred embodiment, an adhesive can be applied to the part of the marker core or to the side of the laminar material which is not the detectable/reflective side, wherein the adhesive can be a liquid adhesive.

After the adhesive has been applied to the part of the marker core, or preferably, to one side of the laminar material, a circumferential area of the laminar material can be held while the part of the marker core is moved towards the laminar material and the surface of the part of the marker core is pressed against the application side of the laminar material. Since the laminar material is elastic to a certain degree, and since tension in the laminar material is maintained by holding the circumferential area of the laminar material, the region of the laminar material abutting the surface of the part of the marker core adapts to said surface without wrinkling.

In order to ensure that the whole of the surface of the part of the marker core is covered with adhesive, so as to hold the laminar material properly, the quality with which the adhesive has been applied can be quantitatively determined by stimulating a fluorescent adhesive in such a way that the presence of adhesive over the whole of the surface of the part of the marker core can be easily determined.

The adhesive used can be an adhesive which can be cured using UV light, such that the adhesive can be cured by applying UV light to the surface of the part of the marker core which the laminar material is glued onto.

In order to ensure that the laminar material is glued onto the surface of the part of the marker core right up to the border with a corresponding part of the marker core, a rim of each of the parts of the marker core can be cut off together with a rim area of the applied laminar material. If the marker is a spherical marker comprising two corresponding parts which each exhibit a hemispherical shape, then the hemispherical shape of each part of the marker core can be obtained by cutting off a rim of each part of the marker core.

This can be performed by a blade which rotates about its axis and in particular also rotates around the circumference of the part of the marker core.

In order to mount the marker onto a particular object, a mounting adaptor must be provided, which is a recess in the surface of one or both parts of the marker core. Once the laminar material has been applied to the parts of the marker core, this recess is covered with the laminar material, thereby losing its function. Therefore, the part of the laminar material extending over the recess must be removed, which in accordance with another preferred embodiment can be achieved by holding a part of the marker core on an engagement surface on a side facing away from the surface to which the laminar material is applied, and moving the part of the marker core towards a cutter which cuts the laminar material. In order to facilitate cutting and removing the part of the laminar material which extends over the recess, the part of the marker core can be rotated as the cutter engages the laminar material. The cutter can be a circular cutter.

Once each part of the marker core has been provided with a layer of the reflective laminar material, the parts are then ready for assembly. The cutting edges obtained by cutting off a rim of each part of the marker core can each serve as an abutting edge, wherein the cutting edges of the parts of the laminar material which have been applied to the parts of the marker core also abut each other, such that the reflective property of the marker is not affected by the cutting edges of the laminar material.

In accordance with a preferred embodiment, the parts of the marker core are glued together. However, any join known to a skilled person can be provided in order to assemble the parts of the marker core, such as for example a positive fit, an adhesive connection or a frictional force-fit connection.

After the parts of the marker core have been assembled to form a marker, the surface quality—in particular, the reflective capability of the assembled marker—can be determined, in particular by detecting defects on the reflective surface, wherein markers which exhibit unacceptable defects are discarded. The quality of the surface can be determined in the same way as the quality of the laminar material provided.

The present invention relates to a multi-part medical marker which can be obtained using the method described above. In accordance with the present invention, a multi-part medical marker is provided which comprises a marker core consisting of at least two corresponding parts and comprising a detectable surface, wherein the surface is substantially formed from a detectable coating which is applied to the surface of the parts of the marker core.

In accordance with a preferred embodiment of the present invention, the detectable coating is a reflective coating, in particular a coating which reflects UV light.

In accordance with another preferred embodiment, the parts of the marker core are made of polyamide and/or polycarbonate and can have a substantially spherical shape.

In accordance with another preferred embodiment, the marker core comprises two parts which exhibit a substantially hemispherical surface, wherein at least one of the parts can be hollow, such that the marker obtained is hollow, so as to save material and reduce the weight of the marker.

In accordance with another preferred embodiment of the present invention, the laminar material is an elastic textile material, in particular a cotton-based fabric which is metallised with aluminium comprising microscopic glass spheres. A laminar material which exhibits an elastic property will adapt to the hemispherical surface of each of the parts of the marker core, without wrinkling, when the hemispherical surface of the parts of the marker core is pressed against the laminar material.

The application side of the laminar material can be glued onto the surface of the parts of the marker core using an adhesive which can be a liquid adhesive, a fluorescent adhesive and/or an adhesive which can be cured by applying UV light.

In order to allow the marker to be fixed to an object which is to be tracked, the marker has a mounting adaptor which can be formed on or in at least one of the parts of the marker core. In accordance with a preferred embodiment of the present invention, the marker is a spherical marker comprising two hemispherical parts, wherein one of the hemispherical parts comprises a mounting adaptor which can be a recess, in particular a blind hole, which extends from the surface of the marker core towards the centre of the marker. In order to ensure that the marker is securely fixed to an object which is to be tracked, the recess can comprise an internal thread, wherein any alternative to a thread which is known to a skilled person can be provided in order to ensure that the marker is securely fixed to an object via the mounting adaptor. In order to facilitate handling the parts of the marker core, at least one of the corresponding parts of the marker core has an engagement surface on its rear side, in particular on the rear side of a first extension on a hollow side of the marker core. The rear side of the marker core is the side of the marker core which faces away from the surface of the marker core and the side to which the reflective material is applied.

In accordance with another preferred embodiment of the present invention, the recess and/or mounting adaptor is formed in said extension from the other side, i.e. from the surface of the part of the marker core. The engagement surface can also be a hexagonal head which can be grasped by a holding device of an apparatus for producing the medical marker.

In accordance with another preferred embodiment of the present invention, at least one of the corresponding parts of the marker core comprises a second extension, in particular a circumferential collar, which is situated in the vicinity of the joint and projects towards the respective other part of the marker core, wherein the second extension is cut off before the corresponding parts of the marker core are joined together. In addition, at least one of the corresponding parts of the marker core comprises a third extension, in particular a circumferential collar, which is situated in the vicinity of the cutting edge, projects towards the respective other part of the marker core and abuts the respective other part of the marker core, in particular at a corresponding recess of said part, in order to facilitate joining the corresponding parts together.

Another aspect disclosed herein relates to an apparatus for producing a medical marker comprising a marker core and a detectable surface, wherein the apparatus comprises a first feeding device for providing the marker core, an application device for applying a detectable layer to the surface of the marker core, and a transport device for transporting the marker core within the apparatus.

In accordance with a preferred embodiment, the medical marker is a multi-part medical marker comprising a marker core consisting of at least two corresponding parts and comprising a detectable surface, wherein the apparatus for producing the multi-part medical marker comprises a first feeding device for providing the parts of the marker core, an application device for applying a detectable layer to the surface of the parts of the marker core, a joining device for joining the parts of the marker core together to form a marker, and a transport device for transporting the parts of the marker core within the apparatus. The first feeding device can comprise a separate feeding port for each kind of part of the marker core. A supply container containing a plurality of a respective kind of part of the marker core can be provided, wherein the feeding port extends from the supply container to the transport device which transports parts of the marker core within the apparatus. Each feeding port carries respective parts of the marker core from the respective supply containers to the transport device for subsequent manufacturing.

The laminar material which is to be applied to the marker core can be provided by a second feeding device, wherein the laminar material can be a ribbon-like material, in particular a textile strip comprising a detectable side.

The second feeding device can also comprise at least one of the following:
- at least one reel support, preferably one reel support for each kind of part of the marker core provided;
- means for determining the surface quality of the detectable side of the laminar material provided, in particular by optical detection; and
- means for cleaning the laminar material provided, in particular a suction-cleaning device which is directed onto at least one side of the laminar material provided and removes contaminants by suctioning.

The application device of the apparatus can also comprise at least one of the following:
- means for applying a liquid adhesive to an application side of the laminar material which is not the detectable side;
- means for holding a circumferential area of the laminar material provided and means for pressing the surface of the parts of the marker core against the application side of the laminar material, in such a way that the tension in the laminar material is maintained and the laminar material adapts to the surface of the part of the marker core, without wrinkling, when the parts of the marker core are pressed against the laminar material;
- means for determining the quality with which the adhesive has been applied, in particular by fluorescently stimulating the adhesive.

The apparatus can also comprise a first curing device for curing the adhesive by applying UV light after the laminar material has been applied to the surface of the part of the marker core, wherein the curing device comprises and is enclosed by a light-proof housing in order to prevent UV light from leaving the curing device. The apparatus can also comprise a second curing device for curing the adhesive by applying UV light after the corresponding parts of the marker core have been joined together, wherein the curing device comprises and is enclosed by a light-proof housing in order to prevent UV light from leaving the curing device.

In order to cut off a rim of the part of the marker core together with a rim area of the laminar material so as to obtain a part of the marker core which exhibits a detectable hemispherical surface, the apparatus can comprise a cutting device which preferably comprises a blade which rotates about its axis and in particular additionally rotates around the circumference of the part of the marker core, thereby cutting off said rims.

In accordance with another preferred embodiment, the apparatus can comprise a joining preparation device which comprises at least one of the following:
- means for removing a part of the laminar material which extends over a recess in the surface of the part of the marker core which serves as a mounting adaptor;
- means for applying an adhesive to at least a cutting edge of at least one of the corresponding parts of the marker core.

An apparatus can be provided which is capable of producing a multi-part medical marker such as has been described herein, wherein said apparatus can perform the method described herein.

Preferred embodiments of the present invention are described with the aid of FIGS. 1 to 6.

FIG. 3 is a second side view of the apparatus shown in FIG. 1;

Figure 1:
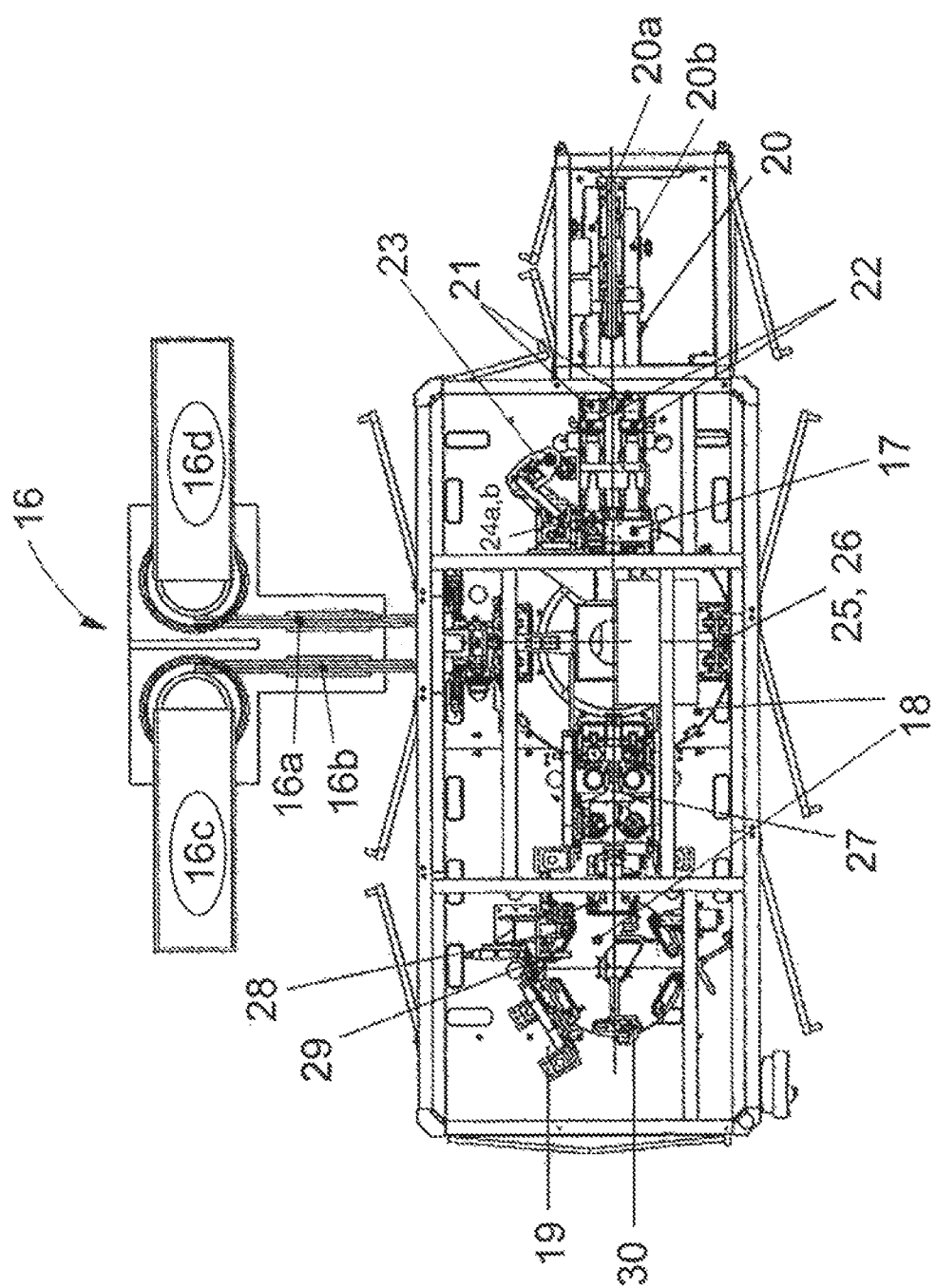
FIG. 1 is a top view of an embodiment of the apparatus disclosed herein.

As can be seen in FIG. 1, two corresponding parts 2a, 2b of a marker core 2 of the multi-part medical marker 1 in accordance with the invention are supported by a first feeding device comprising two separate feeding ports 16a, 16b and are carried from supply containers 16c, 16d to the transport device 18 of the apparatus. Since the hemispherical parts 2a, 2b are transported to the transport device with their hemispherical surface facing upwards but are transported by the transport device 18 with their hemispherical surface directed downwards, the marker core parts 2a, 2b are turned upside down as they are transferred from the first feeding device 16 to the transport device 18. The transport device 18 of the embodiment shown in FIG. 1 comprises two turntables, wherein the first turntable rotates in a clockwise direction and the second turntable rotates in an anti-clockwise direction. When the corresponding parts 2a, 2b are transferred to the first turntable which rotates in a clockwise direction, they are turned upside down by suitable means and placed on adjacently arranged holding adaptors. Once the corresponding parts 2a, 2b have been placed on the holding adaptors, the first turntable rotates over a predetermined angle—in the present embodiment, 90°—such that the corresponding parts 2a, 2b are situated at an application device 17, where an elastic textile material, namely a cotton-based fabric which is metallised with aluminium comprising microscopic glass spheres, is applied to each hemispherical surface of the corresponding parts 2a, 2b. The application device 17 comprises two reel supports 20a, 20b which deliver a strip of reflective material which in the present embodiment consists of "3M Scotchlite® reflective material 8910". The wound strip of reflective material is delivered in a direction towards the left in FIG. 1, thus passing the means 21 for determining the surface quality of the detectable side of the strip, wherein the quality can be determined in the following ways:
- setting a maximum tolerable amount of visible defects, independent of their surface area;
- setting a maximum tolerable surface area for any one defect;
- setting a maximum tolerable surface area of all the defects together;
- setting a maximum tolerable defective surface area for a predetermined surface area; and/or setting a maximum tolerable percentage of defects, wherein the strip of reflective material can pass the quality control process if all or certain tolerance limits are not exceeded.

If one or more tolerance limits are exceeded, then the defective section of the strip will be cut off and discarded. If a section of the strip has passed the quality control process, then cleaning means remove contaminants from the surface of the strip by suctioning, a section of the strip is cut off from the continuous strip, and a certain, predetermined amount of liquid adhesive is applied to the application side of the strip by the adhesive application means 23. The section of the strip with the liquid adhesive 5 on its application side is held in a circumferential area 7 of the strip, while the surface 3 of a part 2a or 2b of the marker core is pressed against the application side of the strip, wherein a corresponding recess beneath the section of the strip accommodates one of the parts 2a, 2b of the marker core together with the reflective material on its surface. The tension in the elastic section of the strip is maintained during this time, such that the section of the strip adapts to the surface 3 of the part 2a, 2b of the marker core without wrinkling. The above process is performed in parallel for the two parts 2a, 2b of the marker core.

The first turntable then turns by another 90°, such that the corresponding parts 2a, 2b are situated in a first curing device 26. Means 25 determine the quality with which the adhesive has been applied, by fluorescently stimulating the adhesive 5 applied to the two parts 2a, 2b of the marker core. Parts of the marker core with unacceptable defects are discarded. The first curing device 26 comprises a housing which is impermeable to UV light, in order to prevent UV light from leaving the curing device 26, wherein the UV light is applied to the parts 2a, 2b of the marker core comprising the reflective material.

Once the adhesive 5 has been cured, the turntable again turns by 90°, such that the corresponding parts 2a, 2b are situated at a cutting device 27 which cuts off a rim of the two parts 2a, 2b of the marker core together with a rim area 7 of the reflective material. When the rim 6 of the parts 2a, 2b of the marker core is cut off, the parts 2a, 2b finally obtain their exact hemispherical shape, and it is then possible to ensure that the adhesive and the reflective material are applied right up to the cutting edge.

The corresponding parts 2a, 2b are transferred by suitable means, preferably by vacuum grasping means from the first turntable to the second turntable which rotates by 60° in each step.

Once the second turntable has rotated by 60°, the parts 2a, 2b—which are held by a holding adaptor of the second turntable—are situated at a joining preparation device, wherein means 28 remove the part of the reflective material which extends over the recess in the surface of the part 2a of the marker core, which serves as the mounting adaptor described further below. This is achieved by grasping the part 2a of the marker core at a hexagonal head 10 which faces away from the reflective surface of the part 2a and moving the part 2a towards a circular cutter which engages the reflective material applied to the surface 3 of the part 2b. Once engaged, the part 2b is turned by the grasping means which engages the hexagonal head 10 such that the circular cutter cuts off a part 8 of the reflective material 4. Means 29 apply an adhesive to the cutting edge of the part 2a of the marker core, and the part 2a is then placed onto the corresponding part 2b which rests beside it.

The marker 1 obtained by joining the parts 2a and 2b is delivered to a second curing device 30 by turning the second turntable by 60°. The second curing device 30 exhibits the same features as the first curing device 26.

Once the adhesive applied to the part 2b has been cured by applying UV light, the marker has been completely manufactured and can be removed from the apparatus.

Within the fully automated apparatus, the parts 2a, 2b and the marker 1 are grasped by vacuum grasping means. Since the apparatus is completely enclosed by a housing, the entire manufacturing process is environmentally isolated and the markers are therefore secured against any microbiological contamination.

Figure 2:
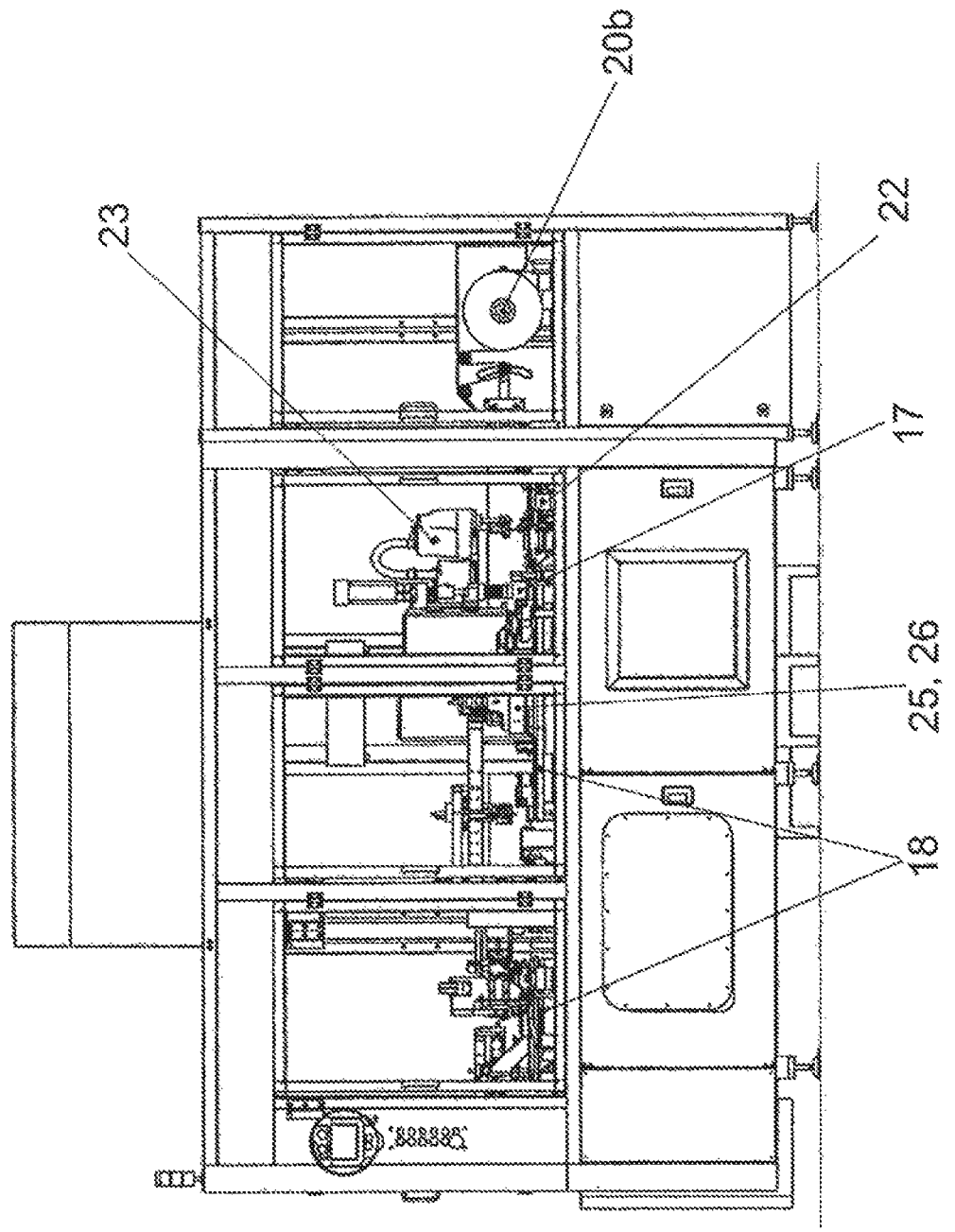
FIG. 2 is a first side view of the apparatus shown in FIG. 1.

FIGS. 2 and 3 show side views of the embodiment of the apparatus as described above.

Figure 4:
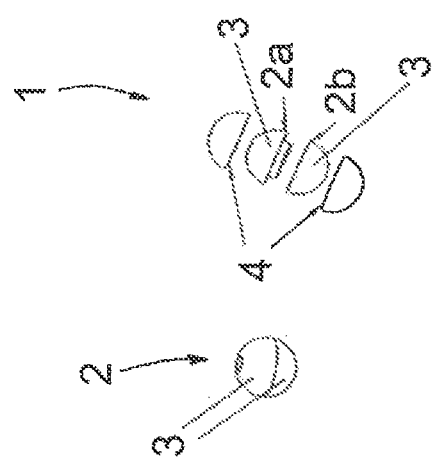
FIG. 4 is an exploded view of an embodiment of the marker in accordance with the invention.

A marker core 2 comprising two corresponding parts 2a, 2b which each exhibit a hemispherical surface 3 is shown on the left in FIG. 4. An exploded view of an embodiment of the marker in accordance with the invention is shown on the right in FIG. 4. The two parts 2a, 2b of the marker core are covered with two hemispherical sections of a reflective material which is glued onto the surface 3 of each part 2a, 2b.

Figure 5:
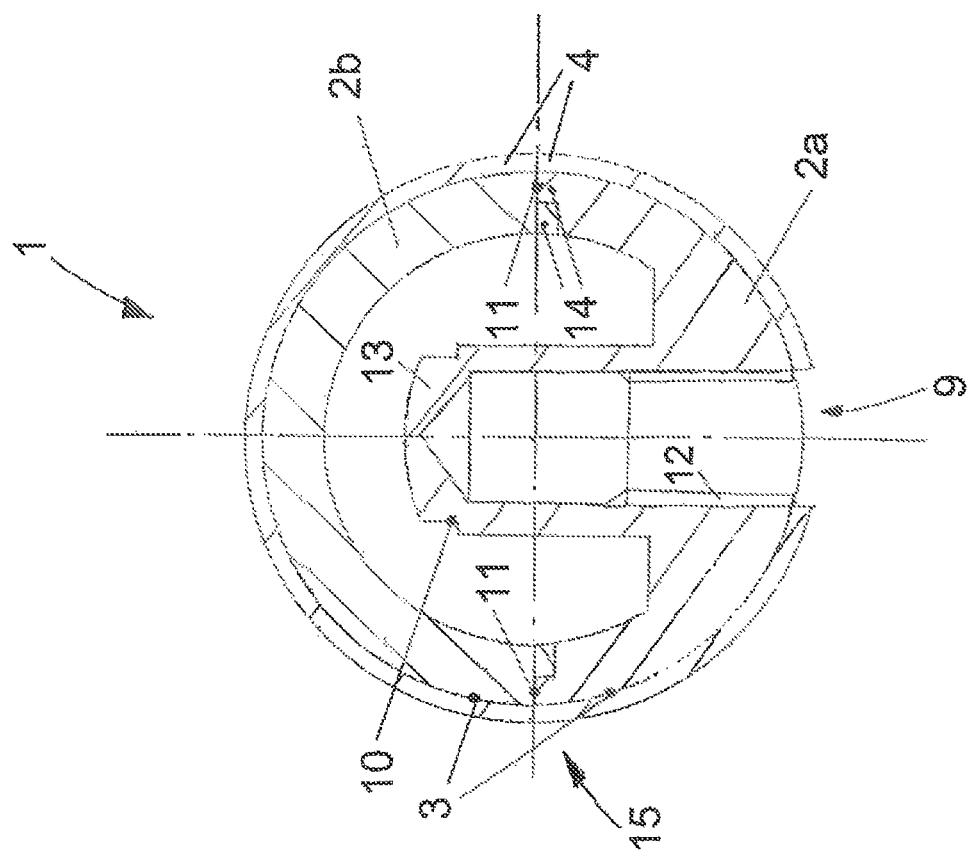
FIG. 5 is a cross-sectional view of the marker shown in FIG. 4.

FIG. 5 shows an embodiment of the marker 1 in accordance with the invention, comprising two corresponding parts 2a, 2b of a marker core 2. Both parts 2a, 2b have a recess on their side facing away from the hemispherical surface 3, such that the marker 1 is a hollow marker. The part 2a has a recess 9 which comprises an internal thread 12 and serves as a mounting adaptor for fixing the marker to an object which is to be tracked. The recess 9 extends into an extension 13 which comprises a hexagonal head 10, such that a grasping device can handle the part 2a by grasping the extension 13 comprising the hexagonal head 10. The two parts 2a, 2b are glued together by applying an adhesive to at least the cutting edge 11. A second extension is not shown in FIG. 5, since the second extension has been cut off from the parts 2a, 2b in order to obtain a hemispherical shape for each of the parts 2a, 2b. A third extension 14 is formed on each of the parts 2a, 2b in order to facilitate joining the parts 2a, 2b together.

Figure 6D:
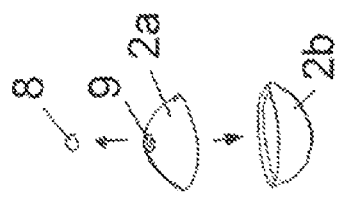
FIGS. 6a to 6d show several steps for manufacturing an embodiment of the marker in accordance with the invention.
Figure 6C:
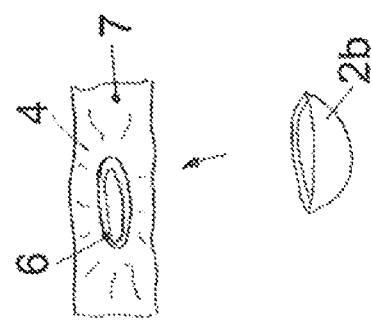
Figure 6B:
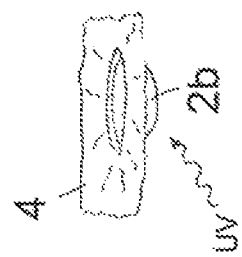
Figure 6A:
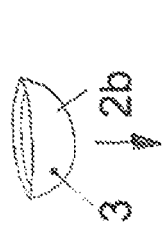

FIG. 6a shows a section of a ribbon-like material 4 which has been supplied in the direction indicated by the arrow, wherein a certain, predetermined amount of adhesive 5 has been applied to a section of an application side of the ribbon-like material 4. The reflective side of the ribbon-like material 4 is the other side which faces away from the viewer in FIG. 6a. The hemispherical surface of a part 2b of the marker core is moved against the application side of the reflective material, such that the reflective material adapts to the hemispherical form of the part 2b due to its elastic properties.

FIG. 6b shows a subsequent step in which the adhesive applied to the reflective material is cured using UV light.

FIG. 6c shows a subsequent step in which a rim 6 of the part 2b is cut off together with a rim area 7 of the reflective material, so as to obtain a hemispherical shape for the part 2b.

FIG. 6d shows a subsequent step in which a part 8 of the reflective material 4, which extends over the recess 9, is removed. As indicated by an arrow, the part 2a is placed onto the part 2b, wherein adhesive has been applied to the cutting edge which results from cutting off the rim 6 together with the rim area 7.

In the following part of the present specification, numbered examples are listed which are directed to advantageous embodiments. These embodiments can represent separate and independent inventions. The embodiments and features listed can be implemented separately or in groups and can be combined in any way to form embodiments which also then form part of the present disclosure.

Numbered Examples 1. A method for producing a multi-part medical marker comprising a marker core consisting of at least two corresponding parts and comprising a detectable surface, said method comprising the following steps:
providing the parts of the marker core; applying a detectable layer to the surface of the parts of the marker core; and joining the parts (2a, 2b) of the marker core together to form a marker.
2. The method according to Example 1, further comprising the following step:
injection-moulding the parts of the marker core.
3. The method according to any one of Examples 1 to 2, further comprising the following step:
providing a laminar material, in particular a ribbon-like material, specifically a textile strip, comprising a detectable side.
4. The method according to any one of Examples 1 to 3, further comprising the following step:
cleaning, in particular vacuum-cleaning, the laminar material provided.
5. The method according to any one of Examples 1 to 4, further comprising the following steps:
determining the surface quality of the detectable side of the laminar material provided, in particular by detecting defects on the surface of the detectable side; and discarding parts of the laminar material which exhibit unacceptable defects.
6. The method according to Example 5, wherein the defects are detected by optical detection.
7. The method according to any one of Examples 1 to 6, further comprising the following step:
cutting off a part of the laminar material to be applied to the surface of a part of the marker core, wherein said part of the laminar material is larger than the surface of the part of the marker core.
8. The method according to any one of Examples 1 to 7, further comprising the following step:
applying an adhesive, in particular a liquid adhesive, to an application side of the laminar material which is not the detectable side.
9. The method according to any one of Examples 1 to 8, further comprising the following step:
holding a circumferential area of the laminar material while pressing the surface of the part of the marker core against the application side of the laminar material, in such a way that the tension in the laminar material is maintained, such that the laminar material adapts to the surface of the part of the marker core, without wrinkling.
10. The method according to any one of Examples 1 to 9, further comprising the following step:
determining the quality with which the adhesive has been applied, in particular by quantitatively determining the area of the surface within which the adhesive is present.
11. The method according to Example 10, wherein the adhesive is fluorescent and the area of the surface within which the adhesive is present can be determined by fluorescently stimulating the adhesive.
12. The method according to any one of Examples 1 to 11, further comprising the following step:
curing the adhesive, in particular by applying UV light, after the laminar material has been applied to the surface of the part of the marker core.
13. The method according to any one of Examples 1 to 12, further comprising the following step:
cutting off a rim of the part of the marker core together with a rim area of the laminar material so as to obtain a part of the marker core which exhibits a detectable hemispherical surface.
14. The method according to Example 13, wherein the rims are cut off by a blade which rotates about its axis and in particular additionally rotates around the circumference of the part of the marker core.
15. The method according to any one of Examples 1 to 14, further comprising the following step:
removing a part of the laminar material which extends over a recess in the surface of the part of a marker core which serves as a mounting adaptor.
16. The method according to Example 15, wherein a part of the marker core comprising a recess which serves as a mounting adaptor is held on an engagement surface on a side facing away from the surface to which the laminar material is applied, in particular a hollow side, so as to move the part of the marker core towards a cutter in order to remove said part of the laminar material, wherein the part of the marker core is in particular rotated as the cutter engages the laminar material.
17. The method according to Example 16, wherein the cutter is a circular cutter.
18. The method according to any one of Examples 1 to 17, wherein the corresponding parts of the marker core are joined together such that they abut each other at least at their respective cutting edges which are formed by cutting off their rims.
19. The method according to any one of Examples 1 to 18, wherein the corresponding parts of the marker core are glued together, in particular at least at their respective cutting edges, to form a marker.
20. The method according to any one of Examples 1 to 19, further comprising the following steps:
determining the quality, in particular the surface quality, of the assembled marker, in particular by detecting defects on the detectable surface; and discarding markers which exhibit unacceptable defects.
21. The method according to Example 20, wherein the defects are detected by optical detection.
22. A multi-part medical marker comprising a marker core consisting of at least two corresponding parts and comprising a detectable surface, wherein the surface is substantially formed from a detectable coating which is applied to the surface of the parts of the marker core.
23. The medical marker according to Example 22, wherein the detectable coating is a reflective coating, in particular a coating which reflects UV light.
24. The medical marker according to any one of Examples 22 to 23, wherein the parts of the marker core are made of polyamide.
25. The medical marker according to any one of Examples 22 to 24, wherein the marker has a substantially spherical shape.
26. The medical marker according to any one of Examples 22 to 25, wherein the marker core comprises two hollow parts which exhibit a substantially hemispherical surface.
27. The medical marker according to any one of Examples 22 to 26, wherein the detectable coating is a laminar material comprising a detectable side and an application side which is to be bonded to the surface of the part of the marker core.
28. The medical marker according to Example 27, wherein the laminar material is an elastic textile material, in particular a cotton-based fabric which is metallised with aluminium comprising microscopic glass spheres.
29. The medical marker according to Example 27 or 28, wherein the application side of the laminar material is glued onto the surface of the part of the marker core using an adhesive.
30. The medical marker according to Example 29, wherein the adhesive is a liquid adhesive.
31. The medical marker according to Example 29 or 30, wherein the adhesive is a fluorescent adhesive.
32. The medical marker according to any one of Examples 29 to 31, wherein the adhesive can be cured by applying UV light.
33. The medical marker according to any one of Examples 22 to 32, wherein at least one of the corresponding parts of the marker core has a mounting adaptor.
34. The medical marker according to Example 33, wherein the mounting adaptor is a recess, in particular a blind hole, which extends from the surface of the marker core towards the centre of the marker.
35. The medical marker according to Example 34, wherein the recess comprises an internal thread.
36. The medical marker according to any one of Examples 22 to 35, wherein at least one of the corresponding parts of the marker core has an engagement surface on its rear side, in particular on the rear side of a first extension on a hollow side of the marker core.
37. The medical marker according to Example 36, wherein the recess is formed in said extension.
38. The medical marker according to Example 36 or 37, wherein the engagement surface is a hexagonal head.
39. The medical marker according to any one of Examples 22 to 38, wherein at least one of the corresponding parts of the marker core comprises a second extension, in particular a circumferential collar, which is situated in the vicinity of the joint and projects towards the respective other part of the marker core, wherein the second extension is cut off before the corresponding parts of the marker core are joined together.
40. The medical marker according to any one of Examples 22 to 39, wherein at least one of the corresponding parts of the marker core comprises a third extension, in particular a circumferential collar, which is situated in the vicinity of the cutting edge, projects towards the respective other part of the marker core and abuts the respective other part of the marker core, in particular at a corresponding recess of said part in order to facilitate joining the corresponding parts together.
41. An apparatus for producing a medical marker comprising a marker core and a detectable surface, comprising:
    a first feeding device for providing the marker core;
    an application device for applying a detectable layer to the surface of the marker core; and
    a transport device for transporting the marker core within the apparatus.
42. The apparatus according to Example 41, wherein the medical marker is a multi-part medical marker comprising a marker core consisting of at least two corresponding parts and comprising a detectable surface, wherein the apparatus comprises:
    a first feeding device for providing the parts of the marker core;
    an application device for applying a detectable layer to the surface of the parts of the marker core;
    a joining device for joining the parts of the marker core together to form a marker; and
    a transport device for transporting the parts of the marker core within the apparatus.
43. The apparatus according to Example 42, wherein the first feeding device comprises a separate feeding port for each kind of part of the marker core and the feeding port extends from a supply container which contains a plurality of a respective kind of part of the marker core to the transport device and carries the parts of the marker core from the supply container to the transport device.
44. The apparatus according to any one of Examples 41 to 43, further comprising:
    a second feeding device for providing a laminar material, in particular a ribbon-like material, specifically a textile strip, comprising a detectable side.
45. The apparatus according to any one of Examples 41 to 44, wherein the second feeding device comprises at least one of the following:
    at least one reel support, preferably one reel support for each kind of part of the marker core provided;
    means for determining the surface quality of the detectable side of the laminar material provided, in particular by optical detection; and
    means for cleaning the laminar material provided, in particular a suction-cleaning device which is directed onto at least one side of the laminar material provided and removes contaminants by suctioning.
46. The apparatus according to any one of Examples 41 to 45, wherein the application device comprises at least one of the following:
    means for applying a liquid adhesive to an application side of the laminar material which is not the detectable side;
    means for holding a circumferential area of the laminar material provided and means for pressing the surface of the parts of the marker core against the application side of the laminar material, in such a way that the tension in the laminar material is maintained and the laminar material adapts to the surface of the part of the marker core, without wrinkling, when the parts of the marker core are pressed against the laminar material;
    means for determining the quality with which the adhesive has been applied, in particular by fluorescently stimulating the adhesive.
47. The apparatus according to any one of Examples 41 to 46, further comprising:
    a first curing device for curing the adhesive by applying UV light after the laminar material has been applied to the surface of the part of the marker core, wherein the curing device comprises and is enclosed by a light-proof housing in order to prevent UV light from leaving the curing device.
48. The apparatus according to any one of Examples 42 to 47, further comprising:
    a cutting device for cutting off a rim of the part of the marker core together with a rim area of the laminar material so as to obtain a part of the marker core which exhibits a detectable hemispherical surface, wherein said device preferably comprises a blade which rotates about its axis and in particular additionally rotates around the circumference of the part of the marker core, thereby cutting off said rims.

49. The apparatus according to any one of Examples 42 to 48, further comprising a joining preparation device which comprises at least one of the following:
   means for removing a part of the laminar material which extends over a recess in the surface of the part of the marker core which serves as a mounting adaptor;
   means for applying an adhesive to at least a cutting edge of at least one of the corresponding parts of the marker core.

50. The apparatus according to any one of Examples 42 to 49, further comprising:
   a second curing device for curing the adhesive by applying UV light after the corresponding parts of the marker core have been joined together, wherein the curing device comprises and is enclosed by a light-proof housing in order to prevent UV light from leaving the curing device.

51. The apparatus according to any one of Examples 41 to 50, wherein said apparatus is capable of producing a multi-part medical marker according to any one of Examples 22 to 40, in particular by performing a method according to any one of Examples 1 to 21.

What is claimed:

1. A multi-part medical marker comprising:
   a spherical marker core comprising two corresponding parts fitted together to form the spherical marker core; and
   a detectable surface formed from a retro-reflective laminar material applied to outer surfaces of the two corresponding parts of the spherical marker core and onto rims of the at least two corresponding parts,
   wherein the rims of the two corresponding parts and rim areas of the retro-reflective laminar material applied to the outer surfaces of the two corresponding parts of the spherical marker core are cut off,
   wherein cutting edges obtained by cutting off the rims of the two corresponding parts and the rim areas of the retro-reflective laminar material applied to the outer surfaces of the two corresponding parts serve as abutting edges where corresponding parts of the retro-reflective laminar material applied to the outer surfaces of the two corresponding parts abut each other,
   wherein a first corresponding part of the two corresponding parts defines an extension disposed at a hollow side of the first corresponding part opposite from the outer surface of the first corresponding part,
   wherein the extension defines a handling engagement section disposed at the hollow side of the first corresponding part,
   wherein the extension defines a recess extending within the extension from the outer surface of the first corresponding part towards a center of the spherical marker core,
   wherein the recess defines an internal thread adapted to engage an associated connecting object thereby configuring the medical marker for selective attachment with an associated object to be tracked using the medical marker.

2. The medical marker according to claim 1, wherein the retro-reflective laminar material comprises:
   an elastic textile material comprising a cotton-based fabric which is metallised with aluminium comprising microscopic glass spheres.

3. The medical marker according to claim 1, wherein the recess defines a blind hole.

4. A medical marker comprising:
   a spherical marker core comprising:
      a first hemispherical part defining a first cutting edge formed by cutting a first rim portion from a first marker core part; and
      a second hemispherical part defining a second cutting edge formed by cutting a second rim portion from a second marker core part; and
   a retro-reflective laminar material carried on outer surfaces of the first and second hemispherical parts,
   wherein rim areas of the retro-reflective laminar material extend to the first and second cutting edges of the first and second hemispherical parts,
   wherein the first and second cutting edges of the first and second hemispherical parts are disposed in mutual abutment,
   wherein the first hemispherical part defines an extension disposed at a hollow side of the first hemispherical part opposite from the outer surface of the first hemispherical part,
   wherein the extension defines a handling engagement section disposed at the hollow side of the first hemispherical part,
   wherein the extension defines a recess extending within the extension from the outer surface of the first hemispherical part towards a center of the spherical marker core,
   wherein the recess defines an internal thread adapted to engage an associated connecting object thereby configuring the medical marker for selective attachment with an associated object to be tracked using the medical marker.

5. The medical marker according to claim 4, wherein the laminar material comprises an elastic textile material comprising a cotton-based fabric metallised with aluminium comprising microscopic glass spheres.

6. The medical marker according to claim 4, wherein the recess defines a blind hole.

7. A medical marker comprising:
   a spherical marker core comprising semi-spherical parts mutually connected together at cutting edges of the semi-spherical parts to form the spherical marker core; and
   a retro reflective laminar material on outer surfaces of the semi-spherical parts,
   wherein rim areas of the retro reflective laminar material extend to the cutting edges of the mutually connected together semi-spherical parts,
   wherein the cutting edges of the retro reflective laminar material are held in mutual abutting alignment,
   wherein a first semi-spherical part of the semi-spherical parts defines an extension disposed at a hollow side of the first semi-spherical part opposite from the outer surface of the first semi-spherical part,
   wherein the extension defines a handling engagement section disposed at the hollow side of the first semi-spherical part,
   wherein the extension defines a recess extending within the extension from the outer surface of the first semi-spherical part towards a center of the spherical marker core,
   wherein the recess defines an internal thread adapted to engage an associated connecting object thereby configuring the medical marker for selective attachment with an associated object to be tracked using the medical marker.

8. The medical marker according to claim 7, wherein the laminar material comprises an elastic textile material comprising a cotton-based fabric metallised with aluminium comprising microscopic glass spheres.

9. The medical marker according to claim 7, wherein the recess defines a blind hole.

* * * * *